US006294519B1

United States Patent
Oeltgen et al.

(10) Patent No.: US 6,294,519 B1
(45) Date of Patent: Sep. 25, 2001

(54) METHOD FOR TREATING ISCHEMIA

(75) Inventors: Peter R. Oeltgen, Winchester; Mark S. Kindy, Lexington, both of KY (US); Paul D. Bishop, Fall City, WA (US)

(73) Assignees: University of Kentucky Research Foundation, Lexington, KY (US); ZymoGenetics, Seattle, WA (US)

( * ) Notice: Subject to any disclaimer, the term of this patent is extended or adjusted under 35 U.S.C. 154(b) by 0 days.

(21) Appl. No.: 09/702,305

(22) Filed: Oct. 31, 2000

Related U.S. Application Data

(62) Division of application No. 09/302,820, filed on Apr. 30, 1999, now abandoned.
(60) Provisional application No. 60/083,866, filed on May 1, 1998.

(51) Int. Cl.$^7$ ............................. A01N 37/18; A61K 38/00
(52) U.S. Cl. ............................. 514/16; 530/300; 514/2
(58) Field of Search ........................ 514/2, 16; 530/350

(56) References Cited

U.S. PATENT DOCUMENTS 5,656,420  8/1997  Chien ..................................... 435/1.2

OTHER PUBLICATIONS

Root RK, et al. Septicemia and Septic Shock, Part Five Infectious Diseases, Section 3 Clinical Syndromes. In Harrison's Principles of Internal Medicine. Author JD Wilson. Ed. 12, vol. 1, pp. 502–507, 1991.*
Leist et al., Activation of the 55 kDa TNF Receptor is Necessary and Sufficient for TNF–Induced Liver Failure, Hepatocyte Apoptosis, and Nitrite Release, The Journal of Immunology, 1995, 154: 1307–1316.
Tsutsui et al., IL–18 Accounts for Both TNF–α–and Fas Ligand–Mediated Hepatotoxic Pathways in Endotoxin–Induced Liver Injury in Mice, The Journal of Immunology, 1997, 159: 3961–3967.
Bohlinger et al., Interleukin–1 and Nitric Oxide Protect Against Tumor Necrosis Factor α–Induced Liver Injury Through Distinct Pathways, Hepatology, 1995; 22: 1829–1837.
Leist et al., Murine Hepatocyte Apoptosis Induced In Vitro and in Vivo by TNF–α Requires Transcriptional Arrest, The Journal of Immunology, 1994, 153: 1778–1788.
Hill et al., Cytokines and Liver Disease, Cytokines in Health and Disease, Second Edition, Revised and Expanded, 27: 401–425 (1997).
Reisine et al., *Opioid Analgesics and Antagonists*, Goodman and Gilman's The Pharmacological Basis of Therapeutics, 9th Ed., 1995, Section III drugs Acting on the Central Nervous System, 23: 521–555.
C. V. Borlongan et al., Delta Opioid Peptide (Dadle) Neuroprotects Against Ischemia–reperfusion Damage in the Striatum and Cerebral Cortex, Society for Neuroscience Abstracts, (1998) vol. 24, No. 1–2, p. 979.
V. Erspamer et al., Deltrophins: A Family of Naturally Occuring Peptides With High Affinity and Selectivity for Opioid Binding Sites, Proceedings of the National Academy of Sciences of USA, vol. 86, No. 13, Jul. 1, 1989, pp. 5188–5192.
Zhao et al., Effects of multiple intracerebroventicular injections of [D–Pen2, D–Pen5] enkephalin and [D–ALa2, Glu4] deltorphin II on tolerance to their analgesic action and on brian gamma opioid receptors, Brain Research, vol. 745, No. 1–2, pp. 243–247, 1997.
Joel J. Schultz et al., Ischemic Preconditioning and Morphine–induced Cardioprotection Involve the Delta Opioid Receptor in the Intact Rat Heart, Journal of Molecular and Cellular Cardiology, No. 29, Jan. 1, 1997, pp. 2187–2195.
Steven F. Bolling et al., Use of "Natural" Hibernation Induction Triggers for Myocardial protection, Annals of Thoracic Surgery, Sep. 1997, 64 (3) 623–627.

\* cited by examiner

*Primary Examiner*—Elizabeth Kemmerer
*Assistant Examiner*—Robert S. Landsman
(74) *Attorney, Agent, or Firm*—Wood, Herron & Evans, LLP

(57) ABSTRACT

A method for treating ischemia by administering deltorphins to a mammal. Deltorphin I SEQ ID NO:1, delntorphin II SEQ ID NO:2 or combinations of deltorphins I SEQ ID NO:1 and II SEQ ID NO:2 may be administered. A deltorphin concentration of about 0.5–20 mg/kg body weight, or alternatively a lower concentration of about 1–1000 μg/kg body weight of the mammal in a physiologically acceptable formulation is administered up to four hours after an ischemic episode. Deltorphins may also be administered prior to or concurrently with onset of ischemia. Cerebral or spinal cord ischemia or ischemic heart disease may be treated using the method of the invention.

25 Claims, No Drawings

SEQUENCE LISTING (1) GENERAL INFORMATION:

(iii) NUMBER OF SEQUENCES: 2

(2) INFORMATION FOR SEQ ID NO: 1:

(i) SEQUENCE CHARACTERISTICS:
       (A) LENGTH: 7 amino acids
       (B) TYPE: amino acid
       (C) STRANDEDNESS: single
       (D) TOPOLOGY: linear (ii) MOLECULE TYPE: peptide (xi) SEQUENCE DESCRIPTION: SEQ ID NO: 1:

Tyr Ala Phe Asp Val Val Gly
1               5

(2) INFORMATION FOR SEQ ID NO: 2:

(i) SEQUENCE CHARACTERISTICS:
       (A) LENGTH: 7 amino acids
       (B) TYPE: amino acid
       (C) STRANDEDNESS: single
       (D) TOPOLOGY: linear (ii) MOLECULE TYPE: peptide (xi) SEQUENCE DESCRIPTION: SEQ ID NO: 2:

Tyr Ala Phe Glu Val Val Gly
1               5

METHOD FOR TREATING ISCHEMIA

This application is a continuation of U. S. application Ser. No. 09/302,820, filed April 30, 1999 now abondoned, which claims the benefit of U. S. provisional application Ser. No. 60/083,866, filed May 1, 1998.

FIELD OF THE INVENTION

The invention relates to the use of deltorphins to treat cerebral ischemia and ischemic heart disease.

BACKGROUND

Tissues deprived of blood and oxygen undergo ischemic necrosis or infarction with possible irreversible organ damage. Cerebral ischemia results from decreased blood and oxygen flow implicating one or more of the blood vessels of the brain. In cerebral ischemia, the individual suffers a stroke with sudden development of a focal neurologic deficit and, in most cases, some degree of brain damage. The decreased blood flow may be due to, for example, an occlusion such as a thrombus or embolus, vessel rupture, sudden fall in blood pressure, change in the vessel lumen diameter due to atherosclerosis, trauma, aneurysm, developmental malformation, altered permeability of the vessel wall or increased viscosity or other quality of the blood. Decreased blood flow may also be due to failure of the systemic circulation and severe prolonged hypotension. Ischemic necrosis of the spinal cord may result in sensory or motor symptoms or both that can be referred to cervical, thoracic or lumbar levels of the spine. Ischemic heart disease results from an imbalance between myocardial oxygen supply and demand. In ischemic heart disease, the individual suffers angina pectoris, acute myocardial infarction or sudden death. The imbalance may be caused by, for example, atherosclerotic obstruction of one or more large coronary arteries, nonatheromatous coronary obstructive lesions such as embolism, coronary ostial stenosis associated with luetic aortitis, coronary artery spasm, congenital abnormalities of the coronary circulation, increased myocardial oxygen demands exceeding the normal supply capabilities as in severe myocardial hypertrophy, reduction in the oxygen carrying capacity of the blood such as in anemia, or as a consequence of inadequate cardiac perfusion pressure due to hypotension from any cause.

Current treatments for ischemia encompass behavioral changes, drug therapy, and/or surgical intervention. Drugs are frequently preferred before resorting to invasive procedures and to provide more immediate relief than long-term behavioral changes. Thus, there is a need for a therapeutic agent which can be useful in treating or preventing ischemia.

SUMMARY OF THE INVENTION

The present invention fills this need by providing a method of treating ischemia in a mammal comprised of administering a pharmaceutically effective amount of a deltorphin to said mammal. The ischemic tissue may be brain, spinal cord or heart.

The present invention is also directed to a method of reducing the effect of an ischemic episode comprised of administering a pharmaceutically effective amount of a deltorphin to said mammal.

The present invention is also directed to a method of treating cerebral or spinal cord ischemia or ischemic heart disease in a mammal comprised of administering a pharmaceutically effective amount of a deltorphin to said mammal.

Preferably, the deltorphin is administered in a pharmaceutical composition at a dosage in the range of about 0.5 mg/kg body weight to about 20 mg/kg body weight, or alternatively lower doses in the range of about 1 µg/kg body weight to about 1000 µg/kg body weight of the mammal.

Preferably, the mammal is a human.

DETAILED DESCRIPTION

Deltorphins are endogenous linear heptapeptides isolated from skin extracts of the South American frog *Phyllomedusa bicolor*. These may be further divided into deltorphin I SEQ ID NO:1 and deltorphin II SEQ ID NO:2 depending on their amino acid sequence. Deltorphin I SEQ ID NO:1 has the amino acid sequence Tyr-Ala-Phe-Asp-Val-Val-Gly-$NH_2$ with alanine as either the L- or D- isomer. Deltorphin II SEQ ID NO:2 has the amino acid sequence Tyr-Ala-Phe-Glu-Val-Val-Gly-$NH_2$ with alanine as either the L- or D-isomer. Either deltorphin I SEQ ID NO:1, deltorphin II SEQ ID NO:2 or a combination of deltorphin I SEQ ID NO:1 and II SEQ ID NO:2 may be used in the invention. Deltorphins may be obtained from frog skin extracts or may be synthesized using a commercial peptide synthesizer such the type available from Applied Biosystems.

Deltorphins can be administered to ameliorate or inhibit damage caused by a stroke. A stroke is the acute neurologic injury caused by one of several pathologic processes involving the blood vessels of the brain. The pathologic process may be intrinsic to the vessel itself such as in arteriosclerosis, or may originate from a remote location such as an embolus, or may result from decreased perfusion or increased blood viscosity with inadequate cerebral blood flow, or may result from the rupture of a vessel in the subarachnoid space or intracerebral tissue.

The main causes of ischemic stroke are thrombosis, vasoconstriction and embolism. Diagnosis of a stroke can be readily made by one of ordinary skill in the art. Signs of stroke include paralysis, slurred speech, general confusion, impairment of gait, cortical sensory loss over toes, foot and leg and urinary incontinence, to name just a few. The diagnosis can be confirmed by cerebral angiography and by a computed axial tomography (CT) scan of the brain.

If a stroke occurs, deltorphins can be administered to limit injury to the brain. The ideal mode of administration is by intraperitoneal (i.p.) or intravenous (i.v.) injection at a dose of about 0.5–20 mg/kg, or alternatively of about 1–1000 µg/kg. Deltorphins can also be administered by subcutaneous or intraarterial injection into the carotid artery, or by direct injection into the brain, e.g, intracerebroventricular injection for dispersion into other areas.

Very often a stroke is caused by a cerebral embolism, the likelihood of which can frequently be predicted. In these cases, the deltorphin can be administered prophylactically to prevent or lessen the amount of brain tissue injured during such an event. Many types of heart disease including cardiac arrhythmias or diseases due to cardiac structural abnormalities may produce cerebral emboli. Atrial fibrillation from any cause, including rheumatic valvular disease, may result in emboli being produced which can migrate into the arteries of the brain. Emboli formation and migration can occur as a result of arteriosclerotic cardiovascular disease and myocardial infarction. Emboli formation is also a definite risk for intracardiac surgery and prosthetic valve replacement. Heart bypass surgery and angioplasty can result in the formation of microemboli which can migrate into the arteries of the brain and cause a series of occlusions in a number of arteries, resulting in mental impairment. Cerebral embolism is also the principal complication in the transplant of artificial hearts. Furthermore, the overall risk of stroke after any type of general surgery is 0.2 to 1 percent. The vegetations of acute and subacute bacterial endocarditis can give rise to emboli which can occlude a major intracranial artery. Thus, when these disease states or surgical procedures are planned or are happening, deltorphins can be administered to prevent brain damage due to any resultant emboli and stroke.

Deltorphins can be administered to ameliorate or prevent ischemic necrosis of the spinal cord. The ischemia may be caused by an endarteritis of surface arteries leading to thrombosis. Atherosclerotic thrombosis of the aorta or dissecting aortic aneurysms may cause infarction of the spinal cord (myelomalacia) by occluding nutrient arteries at cervical, thoracic or lumbar levels, as can paralysis during cardiac surgery requiring clamping of the aorta for more than 30 minutes and aortic arteriography. Infarctive or hemorrhagic vascular lesions of the spinal cord (hematomyelia) may result in the sudden onset of symptoms referable to sensory or motor or both spinal tract lesions.

Deltorphins can also be administered to ameliorate or inhibit damage caused by ischemic heart disease. Ischemic heart disease is a general term for a spectrum of diseases of diverse etiology caused by an imbalance between oxygen supply and demand. The usual cause of the imbalance is atherosclerotic obstruction of large coronary arteries, leading to an absolute decrease in coronary artery blood flow. An imbalance may also result from nonatheromatous coronary obstructive lesions such as embolism, coronary ostial stenosis associated with luetic aortitis, coronary artery spasm, or very uncommonly an arteritis of the coronary vessels. The imbalance may also be due to congenital abnormalities of the coronary circulation, an increase in myocardial oxygen demands exceeding the supply capabilities in a normal coronary circulation, a diminished oxygen-carrying capacity of the blood such as in anemia or in the presence of carboxyhemoglobin (e.g., due to cigarette or cigar smoking), or as a consequence of inadequate perfusion pressure due to hypotension. When ischemic events are transient, they may be associated with angina pectoris; if prolonged, they can lead to myocardial necrosis and scarring with or without the clinical picture of acute myocardial infarction.

Ischemic heart disease may be readily diagnosed by one skilled in the art. There may be predictive changes in the electrocardiogram, since ischemia alters electrical properties of the heart. Such changes include inversion of the T wave and displacement of the ST segment. Another important consequence of myocardial ischemia is electrical instability leading to ventricular tachycardia or ventricular fibrillation. Stress tests and coronary arteriography may also provide diagnostic information. These diagnostic test results may determine the need for deltorphin administration.

Since ischemic heart disease is usually asymptomatic until the extent of coronary artery blockage is well advanced, preventative measures to control risk factors and life style patterns associated with the disease are also recommended. In patients in the symptomatic phase of the disease, meticulous attention to life patterns or risk factors must be given in an attempt to promote lesion regression or at least prevent progression. Risk factors include a positive family history of ischemic heart disease, diabetes, hyperlipidemia, hypertension, obesity and cigarette smoking. Life patterns include sedentary lifestyle, psychosocial tension and certain personality traits.

Deltorphins may be administered to asymptomatic individuals having one or more risk factors and/or life style patterns, or to individuals already in the symptomatic phase of ischemic heart disease to reduce or prevent disease progression. Additionally, deltorphins may be administered to the following patients: those having careers that involve the safety of others (e.g., commercial airline pilots) and that present with questionable symptoms, suspicious or positive noninvasive test results, and in whom there are reasonable doubts about the state of the coronary arteries; males who are 45 or older and females who are 55 or older who will undergo valve replacement and who may or may not have clinical evidence of myocardial ischemia; and those at high risk after myocardial infarction because of the recurrence of angina, heart failure, frequent ventricular premature contractions, or signs of ischemia in the stress test, to name just a few. Deltorphins may be administered either separately or in combination with other cardiac drugs such as nitrates, beta-adrenergic blockers, calcium channel antagonists and/or aspirin and either separately or in combination with fibrinolytic drugs such as tissue plasminogen activator (tPA), streptokinase and urokinase. Use of deltorphins may prolong life and/or reduce or eliminate the need for invasive procedures such as coronary arteriography and coronary artery bypass grafting.

According to the present invention, deltorphins are administered to a mammal to treat cerebral or spinal cord ischemia or ischemic heart disease. Deltorphins may be formulated for administration in an aqueous based liquid such as phosphate buffered saline to form an emulsion, or they may be formulated in an organic liquid such as cyclodextran or dimethylsulfoxide to form a solution. The solution or emulsion may be administered by any route, but it is preferably administered parenterally such as by intravenous, intramuscular, intradermal or intraperitoneal injections.

A preferred deltorphin dose is in the range of about 0.5 mg/kg body weight of the mammal to about 20 mg/kg body weight, or alternatively lower doses of about 1 µg/kg body weight to about 1000 µg/kg body weight of the mammal. The time of administration of a single dose of the deltorphin is preferably up to about four hours after onset of an ischemic episode. However, the deltorphin may be administered concurrently with the onset of an ischemic episode or even prior to onset of ischemia and still produce a therapeutic effect.

Efficacy of deltorphin treatment may be evaluated using noninvasive clinical imaging methods such as magnetic resonance imaging (MRI) of the affected region to determine the size of the damaged area. In cerebral ischemia, it is also possible to assess neurologic deficit by performance on behavioral tests such as cognitive recognition or memory function such as the National Institutes of Health (NIH) stroke scale.

While the specific mechanism of deltorphin action on ischemia is unknown, deltorphins exhibit a specific and reproducible effect on decreasing neurological deficit and cerebral infarct volume. This invention will be further appreciated in light of the following example.

EXAMPLE

A murine model of ischemia/reperfusion injury was used to evaluate the effects of deltorphin on cerebral blood flow, behavioral changes and ischemic infarct volume.

Induction of Ischemia

Ischemia was induced by transient occlusion of the external carotid artery (ECA). Male ICR mice weighing about 30–35 g were anesthetized with an intraperitoneal (i.p.) injection of chloral hydrate (350 mg/kg of body weight) and xylazine (4 mg/kg of body weight). Rectal temperatures were maintained at 37±0.5° C. with a heating pad and incubator. The left femoral artery was cannulated with a PE-10 catheter for measurement of arterial blood pressure, $pO_2$, $pCO_2$ and pH.

A midline incision was made in the skin of the neck and the left common carotid artery (LCCA) was exposed. The ECA, superior thyroid artery (STA) and occipital artery (OA) were isolated. The STA and OA were electrocoagulated using a cautery probe (Baxter Hi Temp Cautery, Baxter Healthcare Corp.) and divided. The base of the ECA was secured with a microsurgical clip, then the distal end of the ECA was ligated with a 6-0 nylon suture and the ECA was cut. A blunted 5-0 blue monofilament nylon suture was placed in the end of the ECA, the surgical clip was removed, then the blunted suture was advanced into the ECA until resistance was detected. The blunted suture was then tightened to prevent both slipping of the internal suture and bleeding. The suture was trimmed and the incision was sealed by suturing the skin. The suture remained in place for varying lengths of time up to 24 h. At the desired time, reperfusion of the brain (restoration of blood flow to the brain) was accomplished by retreating the suture from the ECA.

Mean arterial blood pressure (MABP), $pO_2$, $pCO_2$ and pH were measured before occlusion, 10 min after occlusion and 30 min after reperfusion. Cerebral blood flow was monitored by laser-Doppler flowmetry with a fiber optic probe placed 2 mm posterior and 6 mm lateral to the bregma on the ipsilaterial hemisphere of the brain.

Treatment

Test compounds were the delta opioid DADLE (Tyr-D-Ala-Gly-Phe-D-Leu-enkephalin) and deltorphin I SEQ ID NO:1. For analysis of various test compounds, a solution of the test compound in saline or 1 % cyclodextran was prepared. The test compound in solution was administered by i.p. injection at multiple doses prior to or up to 4 h following ischemic injury.

Control animals (n=8) received i.p. injections of saline or 1% cyclodextran. DADLE-treated animals (n=8) and deltorphin-treated animals (n=8) received 4 mg/kg of either DADLE or deltorphin at each of the following times prior to ischemic injury: 6.5 h, 4.5 h, 2.5 h and 0.5 h. At time 0, animals were subjected to 1 h focal middle cerebral arterial occlusion (MCAO) ischemia and 24 h of reperfusion. Cerebral blood was assessed by laser-Doppler flowmetry with a fiber optic probe prior to ischemia and at 0.5 h, 1 h and 2 h post ischemia. Ischemic volume was measured and animals were assessed for behavior changes using a numerical ranking from 0 to 3 according to the following criteria: 0=no observable deficits (normal); 1 =failure to extend right forepaw upon lifting by the tail (mild); 2 =circling to the contralateral side (moderate); and 3=leaning to the contralateral side at rest or no spontaneous motor activity (severe).

Evaluation of Treatment

Brain infarct volume was measured after 1 h of ischemia and again at 24 h after reperfusion. At the desired endpoint, the animal was euthanized. The brain was immediately removed and placed into a mouse brain matrix (ASI, Warren, MI) and 2 mm sections were made. Brain sections were stained with 2% 2,3,5-triphenyltetrazolium chloride (TTC). Infarct size was determined according to the formula:

(contralateral volume−ipsilaterial undamaged volume)×100/contralateral volume to eliminate the effects of edema. Quantitation of contralateral and ipsilaterial volumes was determined by image analysis using a Scion Image (NIH Image Version 1.59) modified by Scion Corp. and Adobe Photoshop 2.0.1.

Statistical analysis of the volume analysis results was performed using the Student's t-test or analysis of variance (ANOVA) followed by the Bonferroni test. Statistical significance was assigned to comparisons of sections from control versus DADLE- or deltorphin-treated animals with $p<0.05$. Data were expressed as mean±standard error of the mean (SEM).

Results

Prior to DADLE treatment, there were no significant differences in MABP, $pO_2$, $pCO_2$, pH or rectal temperature between control animals and DADLE-treated animals. Upon induction of ischemia by middle cerebral arterial occlusion, both control and DADLE-treated animals had a 20% reduction in cerebral blood flow which was sustained for 1 h during the ischemia. After cessation of ischemia, cerebral blood flow returned to baseline levels within 0.5 h. Post ischemia, there were no significant differences in MABP, $pO_2$, $pCO_2$, pH or rectal temperature between control animals and DADLE-treated animals. No changes occurred in neurological deficits between control animals (1.75±0.18) and DADLE-treated animals (1.73±0.20). Infarct volume was reduced by 12% in DADLE-treated animals (67±9 $mm^2$) compared to control animals (76±12 $mm^2$) after 24 h of reperfusion. However, these differences in infarct volume were not statistically significant.

Prior to deltorphin treatment, there were no significant differences in MABP, $pO_2$, $pCO_2$, pH or rectal temperature between control animals and deltorphin-treated animals. Upon induction of ischemia by middle cerebral arterial occlusion, both control and deltorphin-treated animals had a 25% reduction in cerebral blood flow which was sustained for 1 h during the ischemia. After cessation of ischemia, cerebral blood flow returned to baseline levels within 0.5 h. Post ischemia, there were no significant differences in MABP, $pO_2$, $pCO_2$, pH or rectal temperature between control animals and deltorphin-treated animals. There was, however, a significant ($p<0.05$) decrease in neurological deficits from deltorphin-treated animals (0.44±0.11) versus control animals (1.55±0.19). Additionally, infarct volume was also significantly reduced by 42% in deltorphin-treated animals (45±10 $mm^2$) compared to control animals (73±13 $mm^2$) after 24 h of reperfusion.

A method for treating cerebral or spinal cord ischemia or ischemic heart disease by deltorphin administration is thus disclosed. Deltorphins, either deltorphin I SEQ ID NO:1, deltorphin II SEQ ID NO:2 or a combination of deltorphins I SEQ ID NO:1 and II SEQ ID NO:2 are formulated for biocompatable administration in a preferred dose in the range of about 0.5–20 mg/kg, or alternatively 1–1000 µg/kg body weight of the animal. The deltorphin dose may be administered up to four hours after the onset of an ischemic attack. Alternatively, the deltorphin dose may be administered prophylactically in patients at risk for an ischemic attack such as, for example, prior to surgery. Deltorphin administration reduces the effect of an ischemic event.

It should be understood that the embodiments of the present invention shown and described in the specification are only preferred embodiments of the inventors who are skilled in the art and thus are not limiting in any way. Therefore various changes, modifications or alterations to these embodiments may be made or resorted to without departing from the spirit of the invention and the scope of the following claims.

What is claimed is:

1. A method of treating ischemia in a mammal experiencing ischemia comprising administering a deltorphin selected from the group consisting of deltorphin I represented by SEQ ID NO:1, deltorphin II represented by SEQ ID NO:2 and combinations thereof to the mammal in a parmaceutically acceptable formulation.

2. The method of claim 1 wherein said deltorphin is administered prior to onset of ischemia.

3. The method of claim 1 wherein said deltorphin is administered up to four hours subsequent to onset of ischemia.

4. The method of claim 1 wherein said deltorphin is administered substantially concurrently with onset of ischemia.

5. The method of claim 1 wherein said deltorphin is administered in the formulation selected from the group consisting of a solution, an emulsion and a suspension.

6. The method of claim 1 wherein said deltorphin is administered parenterally.

7. The method of claim 1 wherein said deltorphin is administered at a concentration in the range of about 0.5–20 mg/kg of body weight of said mammal.

8. The method of claim 1 wherein said deltorphin is administered at a concentration in the range of about 1–1000 µg/kg of body weight of said mammal.

9. The method of claim 1 wherein said deltorphin is administered to treat cerebral ischemia.

10. The method of claim 1 wherein said deltorphin is administered to treat ischemic heart disease.

11. The method of claim 1 wherein said deltorphin is administered to treat spinal cord ischemia.

12. A method for treating cerebral ischemia in a mammal experiencing ischemia comprising administering a pharmaceutically effective concentration of a deltorphin selected from the group consisting of deltorphin I represented by SEQ ID NO:1, deltorohin II represented by SEQ ID NO:2 and combinations thereof.

13. A method for reducing effects of an ischemic episode in a mammal experiencing ischemia comprising administering a pharmaceutically effective concentration of a deltorphin selected from the group consisting of deltorphin I represented by SEQ ID NO:1, deltorphin II represented by SEQ ID NO:2 and combinations thereof.

14. The method of claim 13 wherein said deltorphin is administered up to four hour subsequent to said ischemic episode.

15. The method of claim 13 wherein said deltorphin is administered prior to said ischemic episode.

16. The method of claim 13 wherein said deltorphin is administered substantially concurrently with onset of ischemia.

17. A method of inhibiting ischemia in a mammal at risk for ischemia comprising administering a deltorphin selected from the group consisting of deltorphin I represented by SEQ ID NO:1, deltorphin II represented by SEQ ID NO:2 and combinations thereof to the mammal in a pharmaceutically acceptable formulation.

18. The method of claim 17 wherein said deltorphin is administered in the formulation selected from the group consisting of a solution, an emulsion and a suspension.

19. The method of claim 17 wherein said deltorphin is administered parenterally.

20. The method of claim 17 wherein said deltorphin is administered at a concentration in the range of about 0.5–20 mg/kg of body weight of said mammal.

21. The method of claim 17 wherein said deltorphin is administered at a concentration in the range of about 1–1000 µg/kg of body weight of said mammal.

22. The method of claim 17 wherein said deltorphin is administered to prevent cerebral ischemia.

23. The method of claim 17 wherein said deltorphin is administered to prevent ischemic heart disease.

24. The method of claim 17 wherein said deltorphin is administered to prevent spinal cord ischemia.

25. A method for inhibiting ischemia in a mammal at risk for ischemia comprising administering a pharmaceutically effective concentration of a deltorphin selected from the group consisting of deltorphin I represented by SEQ ID NO:1, deltorphin II represented by SEQ ID NO:2 and combinations thereof.

* * * * *

UNITED STATES PATENT AND TRADEMARK OFFICE
CERTIFICATE OF CORRECTION

PATENT NO. : 6,294,519 B1
DATED : September 25, 2001
INVENTOR(S) : Peter R. Oeltgen et al.

It is certified that error appears in the above-identified patent and that said Letters Patent is hereby corrected as shown below:

Title page,
Item [62], Related U.S. Application Data, line 1, change "Division" to
-- Continuation --.
Item [57], ABSTRACT, line 2, change "delntorphin" to -- deltorphin --.

Column 8, claim 12,
Line 38, change "deltorohin" to -- deltorphin --.

Column 9, claim 25,
Line 7, change "inhibiting ischemia in a mammal" to -- inhibiting cerebral ischemia in a mammal --.

Signed and Sealed this

Sixteenth Day of April, 2002

Attest:

JAMES E. ROGAN
*Attesting Officer*   *Director of the United States Patent and Trademark Office*